(12) United States Patent
Guckel et al.

(10) Patent No.: US 7,968,491 B2
(45) Date of Patent: *Jun. 28, 2011

(54) MULTI-LAYER CATALYST FOR PRODUCING PHTHALIC ANHYDRIDE

(75) Inventors: Christian Guckel, Grafing (DE); Markus Niedermeier, Bad Aibling (DE); Marvin Estenfelder, Karlsruhe (DE)

(73) Assignee: Sud-Chemie AG, Munich (DE)

( * ) Notice: Subject to any disclaimer, the term of this patent is extended or adjusted under 35 U.S.C. 154(b) by 296 days.

This patent is subject to a terminal disclaimer.

(21) Appl. No.: 11/914,147

(22) PCT Filed: Nov. 28, 2005

(86) PCT No.: PCT/EP2005/012703
§ 371 (c)(1),
(2), (4) Date: May 16, 2008

(87) PCT Pub. No.: WO2006/125468
PCT Pub. Date: Nov. 30, 2006

(65) Prior Publication Data
US 2009/0306409 A1 Dec. 10, 2009

(30) Foreign Application Priority Data
May 22, 2005 (WO) ............... PCT/EP2005/005548

(51) Int. Cl.
B01J 21/00 (2006.01)
B01J 31/00 (2006.01)
B01J 27/00 (2006.01)
B01J 27/198 (2006.01)
B01J 23/02 (2006.01)

(52) U.S. Cl. ........ 502/350; 502/159; 502/208; 502/209; 502/344; 502/349; 502/353

(58) Field of Classification Search ................. 502/159, 502/208, 209, 344, 349, 350, 353
See application file for complete search history.

(56) References Cited

U.S. PATENT DOCUMENTS

| | | | |
|---|---|---|---|
| 2,035,606 A | 3/1936 | Jaeger | |
| 2,142,678 A | 1/1939 | Porter | |
| 3,684,741 A | 8/1972 | Friedrichsen | |
| 3,799,886 A | 3/1974 | Felice | |
| 3,830,755 A | 8/1974 | Reuter | |
| 3,926,846 A | 12/1975 | Ono | |
| 4,405,505 A | 9/1983 | Neri | |
| 4,489,204 A | 12/1984 | Neri | |
| 5,235,071 A | 8/1993 | Ueda | |
| 5,677,261 A | 10/1997 | Tenten | |
| 5,792,719 A | 8/1998 | Eberle | |
| 5,841,009 A | 11/1998 | Carmello et al. | |
| 5,969,160 A | 10/1999 | Lindstrom | |
| 6,288,273 B1 | 9/2001 | Heidemann | |
| 6,362,345 B1 | 3/2002 | Heidemann | |
| 6,458,970 B1 | 10/2002 | Hefele | |
| 6,586,361 B1 | 7/2003 | Heidemann | |
| 6,700,000 B1 | 3/2004 | Heidemann | |
| 6,774,246 B2 | 8/2004 | Reuter | |
| 7,151,184 B2 | 12/2006 | Storck | |
| 7,390,911 B2 | 6/2008 | Neto | |
| 7,592,293 B2 * | 9/2009 | Guckel et al. | ................. 502/350 |
| 7,615,513 B2 * | 11/2009 | Guckel et al. | ................. 502/350 |
| 7,618,918 B2 * | 11/2009 | Estenfelder et al. | ......... 502/350 |
| 7,718,561 B2 * | 5/2010 | Guckel et al. | ................. 502/20 |
| 2006/0276661 A1 | 12/2006 | Storck | |
| 2007/0060758 A1 | 3/2007 | Storck | |
| 2007/0066836 A1 | 3/2007 | Neto | |
| 2007/0093384 A1 | 4/2007 | Storck | |

(Continued)

FOREIGN PATENT DOCUMENTS

DE 1642938 5/1971

(Continued)

OTHER PUBLICATIONS

Amendment filed Jan. 8, 2009 in response to Office Action dated Oct. 9, 2008 with respect to U.S. Appl. No. 11/817,428, a "potentially related" application disclosed in an Information Disclosure Statement filed on Dec. 18, 2007.

(Continued)

Primary Examiner — Elizabeth D Wood
(74) Attorney, Agent, or Firm — Scott R. Cox

(57) ABSTRACT

The present invention relates to a catalyst for preparing phthalic anhydride by gas phase oxidation of o-xylene and/or naphthalene, comprising at least three catalyst zones which have different compositions and, from the gas inlet side toward the gas outlet side, are referred to as first, second and third catalyst zone, the catalyst zones having in each case an active composition comprising $TiO_2$ with a content of Na of less than 0.3% by weight, and the active composition content decreasing from the first catalyst zone disposed toward the gas inlet side to the third catalyst zone disposed toward the gas outlet side, with the proviso that (a) the first catalyst zone has an active composition content between about 7 and 12% by weight,
(b) the second catalyst zone has an active composition content in the range between 6 and 11% by weight, the active composition content of the second catalyst zone being less than or equal to the active composition content of the first catalyst zone, and
(c) the third catalyst zone has an active composition content in the range between 5 and 10% by weight, the active composition content of the third catalyst zone being less than or equal to the active composition content of the second catalyst zone.

Also described is a preferred process for preparing such a catalyst and the preferred use of the titanium dioxide used in accordance with the invention.

32 Claims, No Drawings

U.S. PATENT DOCUMENTS

2008/0064594 A1    3/2008  Neto

FOREIGN PATENT DOCUMENTS

| DE | 2005969 | 8/1971 |
|---|---|---|
| DE | 19709589 | 9/1998 |
| DE | 102004026472 | 12/2005 |
| EP | 0099431 A1 | 2/1984 |
| EP | 0286448 | 10/1988 |
| EP | 0522871 | 1/1993 |
| EP | 0676400 | 4/1995 |
| EP | 0985648 | 3/2000 |
| GB | 2298197 A | 8/1996 |
| WO | WO2005115615 | 12/2005 |
| WO | WO2005115616 | 12/2005 |

OTHER PUBLICATIONS

Amendment filed Dec. 22, 2008 in response to Office Action dated Sep. 23, 2008 with respect to U.S. Appl. No. 11/575,789, a "potentially related" application disclosed in an Information Disclosure Statement filed on Dec. 18, 2007.

Amendment filed Jan. 20, 2009 in response to Office Action dated Oct. 20, 2008 with respect to U.S. Appl. No. 11/817,362, a "potentially related" application disclosed in an Information Disclosure Statement filed on Dec. 18, 2007.

English translation of International Preliminary Report on Patentability pertaining to international application No. PCT/EP2005/012703, filed in the U.S. under U.S. Appl. No. 11/914,147.

Office Action dated Mar. 9, 2009 with respect to U.S. Appl. No. 11/575,789.

Office Action dated Mar. 10, 2009 with respect to U.S. Appl. No. 11/817,428.

Office Action dated Mar. 23, 2009 with respect to U.S. Appl. No. 11/817,362.

English translation of International Preliminary Report on Patentability pertaining to international application No. PCT/EP2006/001915.

Response filed May 27, 2009 to Office Action dated Mar. 9, 2009 with respect to U.S. Appl. No. 11/575,789, a "potentially related" application disclosed in an Information Disclosure Statement filed on Jan. 7, 2008.

Response filed May 20, 2009 to Office Action dated Mar. 10, 2009 with respect to U.S. Appl. No. 11/817,428, a "potentially related" application disclosed in an Information Disclosure Statement filed on Jan. 7, 2008.

Response filed May 26, 2009 to Office Action dated Mar. 23, 2009 with respect to U.S. Appl. No. 11/817,362, a "potentially related" application disclosed in an Information Disclosure Statement filed on Jan. 7, 2008.

Sadhukhan, R, et al., "Oxidation of Naphthalene in Packed-Bed Reactor with Catalyst Activity Profile: A Design Scheme for Improved Reactor Stability and Higher Product Yield", AIChE Journal, vol. 22, No. 4, 1976, pp. 808-810.

Office Action dated Oct. 9, 2008 with respect to U.S. Appl. No. 11/817,428, a "potentially related" application disclosed in an Information Disclosure Statement filed on Dec. 18, 2007.

Office Action dated Oct. 20, 2008 with respect to U.S. Appl. No. 11/817,362, a "potentially related" application disclosed in an Information Disclosure Statement filed on Dec. 18, 2007.

Office Action dated Sep. 23, 2008 with respect to U.S. Appl. No. 11/575,789, a "potentially related" application disclosed in an Information Disclosure Statement filed on Dec. 18, 2007.

Towae, et al., "Phthalic Acid and Derivatives", Ullmann's Encyclopedia of Industrial Chemistry, vol. A20, 1992, pp. 181-211.

Office Action dated Aug. 17, 2010 with respect to U.S. Appl. No. 11/597,495, a "potentially related" application.

Response dated Nov. 9, 2010 to Office Action dated Aug. 17, 2010 with respect to U.S. Appl. No. 11/597,495, a "potentially related" application.

Office Action dated Jan. 12, 2011 with respect to U.S. Appl. No. 11/597,495, a "potentially related" application.

* cited by examiner

MULTI-LAYER CATALYST FOR PRODUCING PHTHALIC ANHYDRIDE

RELATED APPLICATION

This application is a continuation-in-part application claiming priority from application Ser. No. 11/597,307, with an application filing date of Nov. 20, 2006, which issued as U.S. Pat. No. 7,718,561 on May 18, 2010.

The invention relates to a multi-layer catalyst, i.e. a catalyst having three or more different layers (zones), for preparing phthalic anhydride (PA) by gas phase oxidation of o-xylene and/or naphthalene, the active composition content decreasing from the first catalyst zone disposed toward the gas inlet side to the catalyst zone disposed toward the gas outlet side.

The industrial scale production of phthalic anhydride is achieved by the catalytic gas phase oxidation of o-xylene and/or naphthalene. For this purpose, a catalyst suitable for the reaction is charged into a reactor, preferably what is known as a tube bundle reactor in which a multitude of tubes are arranged in parallel, and is flowed through from the top or bottom with a mixture of the hydrocarbon(s) and an oxygenous gas, for example air. Owing to the intense heat formation of such oxidation reactions, it is necessary for a heat carrier medium to flow around the reaction tubes to prevent what are known as hotspots and thus to remove the amount of heat formed. This energy may be utilized for the production of steam. The heat carrier medium used is generally a salt melt and here preferably a eutectic mixture of $NaNO_2$ and $KNO_3$.

To suppress the unwanted hotspots, it is likewise possible to charge a structured catalyst into the reaction tube, as a result of which, for example, two or three catalyst zones composed of catalysts of different composition can arise. Such systems are as such already known from EP 1 082 317 B1 or EP 1 084 115 B1.

The layer-by-layer arrangement of the catalysts also has the purpose of keeping the content of undesired by-products, i.e. compounds which are before the actual product of value in a possible reaction mechanism of o-xylene to phthalic anhydride, in the crude PA as low as possible. These undesired by-products include mainly the compounds o-tolylaldehyde and phthalide. The further oxidation of these compounds to phthalic anhydride additionally increases the selectivity for the actual product of value.

In addition to the above-addressed under-oxidation products, over-oxidation products also occur in the reaction. These include maleic anhydride, citraconic anhydride, benzoic acid and the carbon oxides. A selective suppression of the formation of these undesired by-products in favour of the product of value leads to a further increase in the productivity and economic viability of the catalyst.

EP 1 084 115 discloses a process for preparing phthalic anhydride by catalytic gas phase oxidation of xylene and/or naphthalene with a molecular oxygen-containing gas in a fixed bed at elevated temperature and by means of at least three coated catalysts arranged one on top of another in layers, to whose core of support material a layer of catalytically active metal oxides has been applied, characterized in that the catalyst activity increases from layer to layer from the gas inlet side to the gas outlet side, the activity of the catalysts of the individual layers being adjusted in such a way that the catalyst having the lowest activity has a lower active composition content and, if appropriate, additionally more alkali metal, selected from the group consisting of potassium, rubidium and caesium, as a dopant than the catalyst of the next layer, and the even more active catalyst which follows has the same amount of active composition and even less alkali metal as a dopant or a larger amount of active composition and, if appropriate, less alkali metal as a dopant than the catalyst of the second layer, with the proviso that a) the catalyst having the lowest activity, on non-porous support material, has 5 to 9% by weight, based on the overall catalyst, of active composition containing 3 to 8% by weight of $V_2O_5$, 0 to 3.5% by weight of $Sb_2O_3$, 0 to 0.3% by weight of P, 0.1 to 0.5% by weight of alkali (calculated as alkali metal) and, as the remainder, $TiO_2$ in anatase form having a BET surface area of 18 to 22 $m^2/g$, b) the next, more active catalyst, with otherwise identical composition to catalyst (a), has an active composition content higher by 1 to 5% by weight (absolute) and the alkali content is lower by 0 to 0.25% by weight (absolute) and c) the most active catalyst, with otherwise identical composition to (a), has an active composition content higher by 1 to 5% by weight (absolute) than for (a) and the alkali content is lower by 0.15 to 0.4% by weight (absolute) than for (a).

A disadvantage of the inventive catalysts specified there is that, in spite of the use of such structured catalysts, very high proportions of the undesired phthalide by-product are still present in the crude PA. It is clear to those skilled in the art that a distillative separation of the two products is possible only with losses of the actual product of value. In addition, the PA yields should be improved.

There is therefore a constant need for improved multi-layer catalysts for the preparation of phthalic anhydride.

It is therefore an object of the present invention to provide an improved catalyst for preparing phthalic anhydride by gas phase oxidation of o-xylene and/or naphthalene, which avoids the disadvantages of the prior art and in particular enables a high selectivity and activity, even after a long operating time.

This object is achieved by the catalyst according to claim 1. Preferred embodiments are specified in the subclaims.

Thus, it has been found that, surprisingly, particularly advantageous catalysts can be prepared when the catalyst is composed of at least three different zones, the active composition content decreasing from the first catalyst zone disposed toward the gas inlet side to the catalyst zone disposed toward the gas outlet side. It has been found to be essential that the first catalyst zone has an active composition content between about 7 and 12% by weight, in particular between about 8 and 11% by weight, the second catalyst zone has an active composition content between about 6 and 11% by weight, in particular between about 7 and 10% by weight, and the third or respectively last catalyst zone has an active composition content between about 5 and 10% by weight, in particular between about 6 and 9% by weight.

The terms first, second and third catalyst zone are used in conjunction with the present invention as follows: the first catalyst zone refers to the catalyst zone disposed toward the gas inlet side. Toward the gas outlet side, the inventive catalyst comprises another two further catalyst zones which are referred to as the second and third catalyst zone. The third catalyst zone is closer to the gas outlet side than the second catalyst zone.

In a particularly preferred inventive embodiment, the inventive catalyst has three catalyst zones. In that case, the third catalyst zone is at the gas outlet side. The presence of additional catalyst zones downstream of the first catalyst zone in the gas flow is, however, not ruled out. For example, in one inventive embodiment, the third catalyst zone as defined herein may be followed downstream by a fourth catalyst zone (having an active composition content equal to or even lower than the third catalyst zone).

According to the invention, the active composition content may decrease between the first and the second catalyst zone and/or between the second and the third catalyst zone.

In a particularly preferred inventive embodiment, the active composition content decreases between the second and the third catalyst zone. It goes without saying that the active composition content never increases in the sequence of the catalyst zones from the gas inlet side to the gas outlet side, but at best remains the same. In a further preferred inventive embodiment the active composition content decreases in the direction of the gas flow from catalyst zone to catalyst zone, i.e. from the first to the last catalyst zone.

It is assumed, without the invention being restricted to the correctness of this assumption, that, as a result of the different layer thicknesses, associated with the different active composition contents, of the catalytically active composition in the individual zones, more preferably the decreasing layer thicknesses of the catalytically active composition from the first to the third zone, influences firstly the reaction of o-xylene up to PA in the first and, if appropriate, second zone, and the remaining under-oxidation products are additionally oxidized in the third zone having the even thinner layer of active composition, for example phthalide to PA, but not PA to the over-oxidation products, for example $CO_x$. As a result, the maximum productivity in the oxidation of o-xylene to PA is achieved over the overall structured packing at a minimum proportion of the undesired by-products.

In a preferred inventive embodiment, the BET surface area increases from the first catalyst zone disposed toward the gas inlet side to the catalyst zone disposed toward the gas outlet side (in particular the third or fourth catalyst zone). As a result, it is surprisingly possible to achieve particularly good catalyst performances. Preferred ranges for the BET surface area are 15 to 25 $m^2$/g for the first catalyst zone, 15 to 25 $m^2$/g for the second catalyst zone and 25 to 45 $m^2$/g for the third (or respectively last) catalyst zone.

In general, it is preferred in accordance with the invention that the BET surface area of the first catalyst zone is lower than the BET surface area of the third (or respectively last) catalyst zone. Particularly advantageous catalysts are also obtained when the BET surface area of the first and of the second catalyst zone is the same, while the BET surface area of the third catalyst zone is greater in comparison. In particular (but not exclusively) when more than three catalyst zones are present, it is also advantageous in a preferred inventive embodiment that the BET surface area of the last catalyst zone disposed toward the gas outlet side is greater than the BET surface area of the catalyst zones disposed closer to the gas inlet side. In a further embodiment, the BET surface area of all catalyst zones apart from the last catalyst zone disposed toward the gas outlet side may be the same.

The catalyst activity toward the gas inlet side is, in a preferred inventive embodiment, lower than the catalyst activity toward the gas outlet side. Thus, the catalyst activity increases from the first to the last zone in this embodiment.

Preferably, the $TiO_2$ used (Anatas modification) (in all catalyst zones) has a content of alkali, especially of Na, of less than 0.3% by weight, preferably less than 0.2% by weight, preferably less than 0.15% by weight, further preferred less than 0.02% by weight, in particular less than 0.015% by weight. The aforementioned threshold values preferably apply to Na and K. In a further preferred inventive embodiment, the proportion of alkali impurities (total alkali content) of the $TiO_2$ used, calculated as the sum of impurities of lithium, sodium, potassium, rubidium and caesium, is less than 1000 ppm, preferably less than 500 ppm, in particular less than 300 ppm. A method for determination of the proportion of alkali impurities of the $TiO_2$ used is given below prior to the examples (DIN ISO 9964-3). The aforementioned total alkali content of $TiO_2$ enables the precise adjustment of the alkali promotor content of the catalyst.

The proportion of alkali impurities, if necessary, may be optionally lowered by washing with diluted nitric acid at elevated temperature, as is known to those skilled in the art, to obtain the preferred range of less than 1000 ppm. The $TiO_2$ may e.g. be slurried in 0.1 M $HNO_3$ and washed under reflux and agitation over night at 90° C., subsequently filtered and washed thrice with bidestillated water and dried at 150° C. in air. Then, the proportion of alkali impurities is determined again and, if found too high, the afore procedure is repeated.

It has also been found that, surprisingly, the inventive multi-layer catalysts with decreasing active composition content can be used particularly advantageously for the preparation of phthalic anhydride when the individual catalyst zones are present in a certain length ratio relative to one another.

In general it has been found that especially good yields of phthalic anhydride may be obtained if the length ratio of the first and second zone is between 1.2 and 5 and that of the lengths of the first and third zone is also between 1.2 and 5. Preferably, the length ratio of the first and second zone is between 2 and 4, in particular between 2.5 and 3.5. Preferably, the length ratio of the first and third zone is between 2 and 4, in particular between 2.5 and 3.5.

Thus, in a particularly preferred inventive embodiment, the first catalyst zone disposed toward the gas inlet side has a length fraction, based on the total length of the catalyst bed, of at least 40%, in particular at least 45%, more preferably at least 50%. It is especially preferred that the proportion of the first catalyst zone in the total length of the catalyst bed is between 40 and 70%, in particular between 40 and 55%, more preferably between 40 and 52%.

The second zone takes up preferably about 10 to 40%, in particular about 10 to 30%, of the total length of the catalyst bed. It has also been found that, surprisingly, a ratio of the length of the third catalyst zone to the length of the second catalyst zone between about 1 and 2, in particular between 1.2 and 1.7, more preferably between 1.3 and 1.6, provides particularly good results with regard to the economic viability, such as the efficiency of raw material utilization and productivity of the catalyst.

It has been found that, as the result of the above selection of the length fractions of the individual catalyst zones, in particular in combination with the decreasing active composition contents as defined above, particularly favourable positioning of the hotspot, in particular in the first zone, and good temperature control for the avoidance of excessively high hotspot temperatures are enabled even at prolonged operating time of the catalyst. As a result, the yield, in particular based on the lifetime of the catalyst, is improved. It is assumed, without the invention being restricted to this assumption, that the above zone length ratio of the individual catalyst zones relative to one another results in virtually full conversion of the o-xylene used actually within the second catalyst zone, and thus, in the third catalyst zone with the above-described advantages, in what is known as "product polishing", i.e. the cleaning of the reaction gas to remove undesired by-products by oxidation to the actual product of value. In addition, it is known to those skilled in the art that, after a certain running time, such catalysts deactivate in the region of the hotspot (generally in the first zone). This deactivation results in a shifting of the reaction into the second, more active zone, which leads to very high hotspot temperatures and the associated problems in relation to selectivity and plant safety. As a result of the zone ratios selected in the inventive catalyst, a maximum residence time of the hotspot in the first zone with the known advantages is ensured, and the inventive length of the second and third zone simultaneously ensures a minimum proportion of undesired by-products with simultaneously maximum yield of actual product of value.

It has also been found that the zone length ratios defined herein also exhibit advantages for other multi-layer catalysts, i.e. which do not have the inventive decrease in the active composition content. In addition to the catalysts for preparing phthalic anhydride (PA) by gas phase oxidation of o-xylene and/or naphthalene, this is also generally the case for other multi-layer catalysts for the gas phase oxidation of hydrocarbons.

The temperature management in the gas phase oxidation of o-xylene to phthalic anhydride is sufficiently well known to those skilled in the art from the prior art, and reference can be made, for example, to DE 100 40 827 A1.

In a further preferred embodiment, the active composition (catalytically active composition) of the inventive catalyst comprises titanium dioxide having a specific BET surface area and preferably a specific pore radius distribution. It has been found that, surprisingly, when titanium dioxide in which at least 25%, in particular at least about 40%, more preferably at least about 50%, most preferably at least about 60%, of the total pore volume is formed by pores having a radius between 60 and 400 nm is used, particularly advantageous catalysts can be obtained.

In a further preferred embodiment, $TiO_2$ is used which has a primary crystal size (primary particle size) of more than about 210 ångstrøm, preferably more than about 250 ångstrøm, more preferably at least 300 ångstrøm, in particular at least about 350 ångstrøm, further preferred at least about 390 ångstrøm. Thus, it has been found that those $TiO_2$ primary crystals having the above (minimum) size enable the preparation of particularly advantageous catalysts. The primary crystal size is preferably below 900 ångstrøm, in particular below 600 ångstrøm, further preferred below 500 ångstrøm. The above primary crystal size apparently enables, without the invention being restricted to this assumption, the formation of a not excessively compact, but rather open-pored structure of the titanium dioxide in the catalyst. One process for determining the primary crystal size is specified in the method section which follows.

In a further preferred embodiment, $TiO_2$ is used which has a bulk density of less than 1.0 g/ml, in particular less than 0.8 g/ml, more preferably less than about 0.6 g/ml. Most preferred are $TiO_2$ materials having a bulk density of not more than about 0.55 g/ml. One process for determining the bulk density is specified in the method section which follows. It has thus been found that the use of titanium dioxide having a bulk density as defined above enables the preparation of particularly high-performance catalysts. It is assumed, without a restriction of the invention thereto, that the bulk density here is a measure of a particularly favourable structure of the $TiO_2$ surface made available in the catalyst, the loose, not excessively compact structure provides particularly favourable reaction spaces, and access and escape routes for the reactants and reaction products respectively.

It is assumed, without the invention being restricted to the correctness of this theoretical assumption, that, as a result of the use of the titanium dioxide having the properties described herein in a catalyst, particularly advantageous reaction spaces can be achieved for the desired reactions, in particular within the pore structure. At the same time, when the inventive $TiO_2$ matrix is used, advantageous access routes for the reactants to the reactive sites on the surface of the $TiO_2$ matrix, and also escape routes for the reaction products, are provided.

In general, when the inventive catalyst is used to prepare phthalic anhydride, a mixture of a molecular oxygen-containing gas, for example air, and the starting material to be oxidized (in particular o-xylene and/or naphthalene) is passed through a fixed bed reactor, in particular a tube bundle reactor, which may consist of a multitude of tubes arranged in parallel. In the reactor tubes is disposed in each case a bed of at least one catalyst. The preferences for a bed composed of a plurality of (different) catalyst zones have already been addressed above.

When the inventive catalysts are used for preparing phthalic anhydride by gas phase oxidation of o-xylene and/or naphthalene, it has been found that, surprisingly, very good PA yields are achieved with the inventive catalysts at very low contents of phthalide.

In a preferred inventive embodiment, the $TiO_2$ used has a BET surface area of at least 15 m$^2$/g, preferably between 15 and 60 m$^2$/g, in particular between about 15 and 45 m$^2$/g and more preferably between 15 and 30 m$^2$/g. The BET surface of the catalyst zone is largely determined by the BET surface of the $TiO_2$ used. In one inventive embodiment, the BET surface of the catalyst zone is therefore equated with the BET surface of the respective $TiO_2$.

It is further preferred that up to 80%, preferably up to 75%, in particular up to 70% of the total pore volume of the $TiO_2$ is formed by pores having a radius between 60 and 400 nm.

The pore volumes and fractions reported herein, unless stated otherwise, are determined by means of mercury porosimetry (to DIN 66133). The total pore volume reported is based in the present description in each case on the total pore volume, measured by means of mercury porosimetry, between 7500 and 3.7 nm pore radius size.

Pores having a radius of more than 400 nm constitute preferably less than about 30%, in particular less than about 22%, more preferably less than 20%, of the total pore volume of the $TiO_2$ used.

It is further preferred that about 50 to 75%, in particular about 50 to 70%, more preferably from 50 to 65%, of the total pore volume of the $TiO_2$ is formed by pores having a radius of 60 to 400 nm, and preferably about 15 to 25% of the total pore volume by pores having a radius of more than 400 nm.

With regard to the smaller pore radii, it is preferred that less than 30%, in particular less than 20%, of the total pore volume of the $TiO_2$ is formed by pores having a radius of 3.7 to 60 nm. For this pore size, a range which is particularly preferred here is about 10 to 30% of the total pore volume, in particular 12 to 20%.

In a further preferred embodiment, the $TiO_2$ used has the following particle size distribution: the $D_{10}$ value is preferably 0.5 μm or lower; the $D_{50}$ value (i.e. the value at which in each case half of the particles have a greater or smaller particle diameter) is preferably 1.5 μm or less; the $D_{90}$ value is preferably 4 μm or less. The $D_{90}$ value of the $TiO_2$ used is preferably between about 0.5 and 20 μm, in particular between about 1 and 10 μm, more preferably between about 2 and 5 μm.

In electron micrographs, the $TiO_2$ used in accordance with the invention preferably has an open-pored, sponge-like structure. The primary crystals are preferably combined to form preferably open-pored agglomerates to an extent of more than 30%, in particular more than 50%. It is assumed, without the invention being restricted to this assumption, that this particular structure of the $TiO_2$ used, which is reflected in the pore radius distribution, provides particularly favourable reaction conditions for the gas phase oxidation.

In a further preferred inventive embodiment the first catalyst zone does not contain phosphorus. It is further preferred that also the second catalyst zone does not contain phosphorus. It is particularly preferred that only the last catalyst layer contains phosphorus, preferably between 0.01 and 0.5% by weight, in particular between 0.1 and 0.4% by weight phosphorus (calculated as phosphorus).

Depending on the intended use of the inventive catalyst, the customary components familiar to those skilled in the art may be present in the active composition of the catalyst in addition to the $TiO_2$ used in accordance with the invention. The shape of the catalyst and its homogeneous or heterogeneous structure are also in principle not restricted in the context of the present invention and may include any embodiment which is familiar to those skilled in the art and appears to be suitable for the particular field of application.

For the preparation of phthalic anhydride, coated catalysts in particular have been found to be useful. For these catalysts, a support which is inert under the reaction conditions, for example composed of quartz ($SiO_2$), porcelain, magnesium oxide, tin dioxide, silicon carbide, rutile, clay earth ($Al_2O_3$), aluminium silicate, magnesium silicate (steatite), zirconium silicate or cerium silicate, or composed of mixtures of the above materials, is used. The support may, for example, have the shape of rings, spheres, shells or hollow cylinders. To this is applied, in comparatively thin layers (shells), the catalytically active composition. It is also possible to apply two or more layers of catalytically active composition having the same or different compositions.

With regard to the further components of the catalytically active composition of the inventive catalyst (in addition to $TiO_2$), it is possible in principle to refer to the compositions and components which are described in the relevant prior art and are familiar to those skilled in the art. They are mainly catalyst systems which, in addition to titanium oxide(s), comprise oxides of vanadium. Such catalysts are described, for example, in EP 0 964 744 B1, whose disclosure on this subject is hereby incorporated explicitly by reference into the description.

In particular, the prior art describes a series of promoters for increasing the productivity of the catalysts, which may likewise be used in the inventive catalyst. These include the alkali metals and alkaline earth metals, thallium, antimony, phosphorus, iron, niobium, cobalt, molybdenum, silver, tungsten, tin, lead and/or bismuth, and mixtures of two or more of the above components. For example, DE 21 59 441 A describes a catalyst which, in addition to titanium dioxide of the anatase modification, consists of 1 to 30% by weight of vanadium pentoxide and zirconium dioxide. It is possible via the individual promoters to influence the activity and selectivity of the catalysts, in particular by lowering or increasing the activity. The selectivity-increasing promoters include, for example, the alkali metal oxides, whereas oxidic phosphorus compounds, in particular phosphorus pentoxide, increase the activity of the catalyst at the cost of the selectivity.

For the preparation of the inventive catalysts, the prior art describes numerous suitable processes, so that a detailed description is in principle not required here. For the preparation of coated catalysts, reference can be made, for example, to the process described in DE-A-16 42 938 or DE-A 17 69 998, in which a solution or suspension, comprising an aqueous and/or an organic solvent, of the components of the catalytically active composition and/or their precursor compounds (frequently referred to as "slurry") are sprayed onto the support material in a heated coating drum at elevated temperature until the desired content of catalytically active composition, based on the total catalyst weight, has been achieved. It is also possible, according to DE 21 06 796, to carry out the application (coating) of the catalytically active composition to the inert support in fluidized bed coaters.

Preference is given to preparing coated catalysts by the application of a thin layer of 50 to 500 μm of the active components to an inert support (for example U.S. Pat. No. 2,035,606). In a preferred inventive embodiment, the thickness of each coated layer (with the active composition) decreases according to the decrease of the active composition content as described herein from the first to the last catalyst zone. If the active composition of the layers decreases, it is preferred that also the thickness of the active composition decreases accordingly. Useful supports have been found to be in particular spheres or hollow cylinders. These shaped bodies give rise to a high packing density at low pressure drop and reduce the risk of formation of packing faults when the catalyst is charged into the reaction tubes.

The molten and sintered shaped bodies have to be heat-resistant within the temperature range of the reaction as it proceeds. As detailed above, possible substances are, for example, silicon carbide, steatite, quartz, porcelain, $SiO_2$, $Al_2O_3$ or clay earth.

The advantage of the coating of support bodies in a fluidized bed is the high uniformity of the layer thickness, which plays a crucial role for the catalytic performance of the catalyst. A particularly uniform coating is obtained by spraying a suspension or solution of the active components onto the heated support at 80 to 200° C. in a fluidized bed, for example according to DE 12 80 756, DE 198 28 583 or DE 197 09 589. In contrast to the coating in coating drums, it is also possible, when hollow cylinders are used as the support, to uniformly coat the inside of the hollow cylinders in the fluidized bed processes mentioned. Among the abovementioned fluidized bed processes, the process according to DE 197 09 589 in particular is advantageous, since the predominantly horizontal, circular motion of the supports achieves not only a uniform coating but also low abrasion of apparatus parts.

For the coating operation, the aqueous solution or suspension of the active components and of an organic binder, preferably a copolymer of vinyl acetate/vinyl laurate, vinyl acetate/ethylene or styrene/acrylate, is sprayed via one or more nozzles onto the heated, fluidized support. It is particularly favourable to introduce the spray liquid at the point of the highest product speed, as the result of which the sprayed substance can be distributed uniformly in the bed. The spray operation is continued until either the suspension has been consumed or the required amount of active components has been applied on the support.

In a particularly preferred inventive embodiment, the catalytically active composition of the inventive catalyst is applied in a moving bed or fluidized bed with the aid of suitable binders, so that a coated catalyst is obtained. Suitable binders include organic binders familiar to those skilled in the art, preferably copolymers, advantageously in the form of an aqueous dispersion, of vinyl acetate/vinyl laurate, vinyl acetate/acrylate, styrene/acrylate, vinyl acetate/maleate and vinyl acetate/ethylene. Particular preference is given to using an organic polymeric or copolymeric adhesive, in particular a vinyl acetate copolymer adhesive, as the binder. The binder used is added in customary amounts to the catalytically active composition, for example at about 10 to 20% by weight based on the solids content of the catalytically active composition. For example, reference can be made to EP 744 214. When the catalytically active composition is applied at elevated temperatures of about 150° C., it is also possible, as is known from the prior art, to apply to the support without organic binders. Coating temperatures which can be used when the above-specified binders are used are, according to DE 21 06 796, for example, between about 50 and 450° C. The binders used burn off within a short time in the course of baking-out of the catalyst when the charged reactor is put into operation. The binders serve primarily to reinforce the adhesion of the catalytically active composition on the support and to reduce attrition in the course of transport and charging of the catalyst.

Further possible processes for preparing coated catalysts for the catalytic gas phase oxidation of aromatic hydrocarbons to carboxylic acids and/or carboxylic anhydrides have been described, for example, in WO 98/00778 and EP-A 714 700. According to these, from a solution and/or a suspension of the catalytically active metal oxides and/or their precursor compounds, optionally in the presence of assistants for the catalyst preparation, a powder is prepared initially and is subsequently, for the catalyst preparation on the support, optionally after conditioning and also optionally after heat treatment, applied in coating form to generate the catalytically active metal oxides, and the support coated in this way is subjected to a heat treatment to generate the catalytically active metal oxides or to a treatment to remove volatile constituents.

Suitable conditions for carrying out a process for preparing phthalic anhydride from o-xylene and/or naphthalene are equally familiar to those skilled in the art from the prior art. In particular, reference is made to the comprehensive description in K. Towae, W. Enke, R. Jäckh, N. Bhargana "Phthalic Acid and Derivatives" in Ullmann's Encyclopedia of Industrial Chemistry Vol. A. 20, 1992, 181, and this is hereby incorporated by reference. For example, the boundary conditions known from the above reference of WO-A 98/37967 or of WO 99/61433 may be selected for the steady operating state of the oxidation.

To this end, the catalysts are initially charged into the reaction tubes of the reactor, which are thermostated externally to the reaction temperature, for example by means of salt melts. The reaction gas is passed over the thus prepared catalyst charge at temperatures of generally 300 to 450° C., preferably 320 to 420° C., and more preferably of 340 to 400° C., and at an elevated pressure of generally 0.1 to 2.5 bar, preferably of 0.3 to 1.5 bar, with a space velocity of generally 750 to 5000 h$^{-1}$.

The reaction gas fed to the catalyst is generally generated by mixing a molecular oxygen-containing gas which, apart from oxygen, may also comprise suitable reaction moderators and/or diluents such as steam, carbon dioxide and/or nitrogen with the aromatic hydrocarbon to be oxidized, and the molecular oxygen-containing gas may generally contain 1 to 100 mol %, preferably 2 to 50 mol % and more preferably 10 to 30 mol %, of oxygen, 0 to 30 mol %, preferably 0 to 10 mol %, of steam, and 0 to 50 mol %, preferably 0 to 1 mol %, of carbon dioxide, remainder nitrogen. To generate the reaction gas, the molecular oxygen-containing gas is generally charged with 30 to 150 g per m$^3$ (STP) of gas of the aromatic hydrocarbon to be oxidized.

In a particularly preferred inventive embodiment, the inventive catalyst has an active composition content between about 7 and 12% by weight, preferably between 8 and 10% by weight, the active composition (catalytically active composition) containing between 5 and 15% by weight of $V_2O_5$, 0 and 4% by weight of $Sb_2O_3$, 0.2 and 0.75% by weight of Cs, 0 and 3% by weight of $Nb_2O_5$. Further to the aforementioned components, the rest of the active composition contains at least 90% by weight, preferably at least 95% by weight, further preferred at least 98% by weight, in particular at least 99% by weight, further preferred at least 99.5% by weight, in particular 100% by weight of $TiO_2$. Such an inventive catalyst may, for example, advantageously be used in a two-zone or multilayer catalyst as the first catalyst zone disposed toward the gas inlet side.

In a particularly preferred inventive embodiment, the BET surface area of the catalyst is between 15 and about 25 m$^2$/g. It is further preferred that such a first catalyst zone has a length fraction of about 40 to 60% in the total length of all catalyst zones present (total length of the catalyst bed present).

In a further preferred inventive embodiment, the inventive catalyst has an active composition content of about 6 to 11% by weight, in particular 7 to 9% by weight, the active composition containing 5 to 15% by weight of $V_2O_5$, 0 to 4% by weight of $Sb_2O_3$, 0.05 to 0.3% by weight of Cs, 0 to 2% by weight of $Nb_2O_5$. Further to the aforementioned components, the rest of the active composition contains at least 90% by weight, preferably at least 95% by weight, further preferred at least 98% by weight, in particular at least 99% by weight, further preferred at least 99.5% by weight, in particular 100% by weight of $TiO_2$. Such an inventive catalyst may, for example, be used advantageously as the second catalyst zone, i.e. downstream of the first catalyst zone disposed toward the gas inlet side (see above). It is preferred that the catalyst has a BET surface area between about 15 and 25 m$^2$/g. It is further preferred that this second zone has a length fraction of about 10 to 30% of the total length of all catalyst zones present.

In a further inventive embodiment, the inventive catalyst has an active composition content between about 5 and 10% by weight, in particular between 6 and 8% by weight, the active composition (catalytically active composition) containing 5 to 15% by weight of $V_2O_5$, 0 to 4% by weight of $Sb_2O_3$, 0 to 0.1% by weight of Cs, 0 to 1% by weight of $Nb_2O_5$. Further to the aforementioned components, the rest of the active composition contains at least 90% by weight, preferably at least 95% by weight, further preferred at least 98% by weight, in particular at least 99% by weight, further preferred at least 99.5% by weight, in particular 100% by weight of $TiO_2$. Such an inventive catalyst may be used, for example, advantageously as the third (or respectively last) catalyst zone disposed downstream of the above-described second catalyst zone. Preference is given to a BET surface area of the catalyst which is somewhat higher than that of the layers disposed closer to the gas inlet side, in particular in the range between about 25 and about 45 m$^2$/g. It is further preferred that such a third catalyst zone has a length fraction of about 10 to 50% of the total length of all catalyst zones present.

It is further preferred in accordance with the invention that, when the inventive catalyst is used in a multi-layer catalyst bed, the content of alkali metals in the catalyst zones falls from the gas inlet side toward the gas outlet side. In a particularly preferred embodiment, the alkali content, especially the Cs-content (calculated as Cs) in the second catalyst zone is less than in the first catalyst zone, and in the third catalyst zone less than in the second catalyst zone (and preferably, if applicable, in the zones following the third zone). It is therefore particularly preferred that the Cs-content (calculated as Cs) in the inventive catalyst decreases from zone to zone in the direction of the gas flow. In a preferred embodiment the third (and, if applicable, also further catalyst zones) do not contain Cs. It is preferred that:

$$\text{Cs-content}_{1st\ zone} > \text{Cs-content}_{2nd\ zone} > \ldots > \text{Cs-content}_{last\ zone}.$$

It is particularly preferred that the last catalyst zone does not contain Cs.

In principle, it is possible in the inventive catalyst also to use a different titanium dioxide with a different specification than described above, i.e. a different BET surface area, porosimetry and/or particle size distribution. However, it is particularly preferred in accordance with the invention that at least 50%, in particular at least 75%, more preferably all, of the $TiO_2$ used has a BET surface area and porosimetry as defined herein, and preferably also the particle size distribution described. It is also possible to use blends of different $TiO_2$ materials.

It has also been found that, in a preferred embodiment, in accordance with the invention, catalysts which do not have any phosphorus in the catalytically active composition in combination with the $TiO_2$ used in accordance with the invention enable particularly good activities at simultaneously very high selectivity. It is further preferred that at least 0.05% by weight of the catalytically active composition is formed by at least one alkali metal, calculated as alkali metal(s). The particularly preferred alkali metal is caesium.

In addition, according to the inventor's results, in one embodiment, it is preferred that the inventive catalyst contains niobium in an amount of 0.01 to 2% by weight, in particular 0.5 to 1% by weight, of the catalytically active composition.

The inventive catalysts are typically thermally treated or calcined (conditioned) before use. It has been found to be advantageous when the catalyst is calcined in an $O_2$-containing gas, in particular in air, at least 390° C. for at least 24 hours, in particular at $\geq$400° C. for between 24 and 72 hours. The temperature should preferably not exceed 500° C., in particular 470° C. In principle, however, other calcination conditions which appear to be suitable to those skilled in the art are also not ruled out.

In a further aspect, the present invention relates to a process for preparing a catalyst as described hereinbefore, comprising the following steps:
   a. providing a catalytically active composition as defined herein,
   b. providing an inert support, in particular an inert shaped support body;
   c. applying the catalytically active composition to the inert support, in particular in a fluidized bed or a moving bed.

In a further aspect, the invention also relates to a process for preparing phthalic anhydride by gas phase oxidation of o-xylene and/or naphthalene, by using a three-layer or multi-layer catalyst as defined in the present description.

In a further aspect, the present invention finally also relates to the use of a catalyst as defined herein for preparing phthalic anhydride by gas phase oxidation of o-xylene and/or naphthalene.

Methods

To determine the parameters of the inventive catalysts, the methods which follow are used:

1. BET Surface Area:
   The determination is effected by the BET method according to DIN 66131; a publication of the BET method can also be found in J. Am. Chem. Soc. 60, 309 (1938).

2. Pore Radius Distribution:
   The pore radius distribution and the pore volume of the $TiO_2$ used were determined by means of mercury porosimetry to DIN 66133; maximum pressure: 2000 bar, Porosimeter 4000 (from Porotec, Germany), according to the manufacturer's instructions.

3. Primary Crystal Sizes:
   The primary crystal sizes were determined by powder X-ray diffractometry. The analysis was carried out with an instrument from Bruker, Germany: BRUKER AXS-D4 Endeavor. The resulting X-ray diffractograms were recorded with the "DiffracPlus D4 Measurement" software package according to the manufacturer's instructions, and the half-height width of the 100% refraction was evaluated with the "DiffracPlus Evaluation" software by the Debye-Scherrer formula according to the manufacturer's instructions in order to determine the primary crystal size.

4. Particle Sizes:
   The particle sizes were determined by the laser diffraction method with a Fritsch Particle Sizer Analysette 22 Economy (from Fritsch, Germany) according to the manufacturer's instructions, also with regard to the sample pretreatment: the sample is homogenized in deionized water without addition of assistants and treated with ultrasound for 5 minutes.

5. Alkali Content of $TiO_2$:
   The alkali content of $TiO_2$ is determined by DIN ISO 9964-3. Thus, an alkali determination is made by ICP-AES (inductively Coupled Plasma Atomic Emission Spectroscopy) and, if applicable, the total alkali content of $TiO_2$ is added up.

6. Bulk Density:
   The bulk density was determined with the aid of the $TiO_2$ used to prepare the catalyst (dried at 150° C. under reduced pressure, uncalcined). The resulting values from three determinations were averaged.
   The bulk density was determined by introducing 100 g of the $TiO_2$ material into a 1000 ml container and shaken for approx. 30 seconds (if required, several parallel batches).
   A measuring cylinder (capacity precisely 100 ml) is weighed empty to 10 mg. Above it, the powder funnel is secured over the opening of the cylinder using a clamp stand and clamp. After the stopwatch has been started, the measuring cylinder is charged with the $TiO_2$ material within 15 seconds. The spatula is used to constantly supply more filling material, so that the measuring cylinder is always slightly overfilled. After 2 minutes, the spatula is used to level off the excess, care being taken that no pressing forces compress the material in the cylinder. The filled measuring cylinder is brushed off and weighed.
   The bulk density is reported in g/ml.

The BET surface area, the pore radius distribution and the pore volume, and also the particle size distribution were determined for the titanium dioxide in each case on the uncalcined material dried at 150° C. under reduced pressure.

The data in the present description with regard to the BET surface areas of the catalysts or catalyst zones also relate to the BET surface areas of the $TiO_2$ material used in each case (dried at 150° C. under reduced pressure, uncalcined, see above).

In general, the BET surface area of the catalyst is determined by virtue of the BET surface area of the $TiO_2$ used, although the addition of further catalytically active components does change the BET surface area to a certain extent. This is familiar to those skilled in the art.

The active composition content (content of the catalytically active composition, without binder) relates in each case to the content (in % by weight) of the catalytically active composition in the total weight of the catalyst including support in the particular catalyst zone, measured after conditioning at 400° C. over 4 h.

The invention will now be illustrated in detail with reference to the non-restrictive examples which follow:

EXAMPLES

Example 1

Preparation of Catalyst A

To prepare catalyst A having an active composition content of 8% by weight and the composition of 7.5% by weight of vanadium pentoxide, 3.2% by weight of antimony trioxide, 0.40% by weight of caesium (calculated as caesium), 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 17.9 g of vanadium pentoxide, 7.6 g of antimony trioxide, 1.3 g of caesium sulphate, 1.9 g of ammonium dihydrogenphosphate, 211.1 g of titanium dioxide having a BET surface area of 21 m$^2$/g, 130.5 g of binder composed of a 50% dispersion of water and vinyl acetate/ethylene copolymer (Vinnapas® EP 65 W, from Wacker) and 2000 g of water. The active composition was applied in the form of thin layers.

Example 2

Preparation of Catalyst B

To prepare catalyst B having an active composition content of 8% by weight and the composition of 7.5% by weight of vanadium pentoxide, 3.2% by weight of antimony trioxide, 0.20% by weight of caesium (calculated as caesium), 0.2% by weight of phosphorus (calculated as phosphorus) and remainder titanium dioxide, 2200 g of steatite bodies in the form of hollow cylinders of size 8×6×5 mm were coated at a temperature of 70° C. in a fluidized bed coater with a suspension of 15.4 g of vanadium pentoxide, 6.6 g of antimony trioxide, 0.5 g of caesium carbonate, 1.5 g of ammonium dihydrogenphosphate, 182.9 g of titanium dioxide having a BET surface area of 21 m$^2$/g, 110.7 g of binder composed of a 50% dispersion of water and vinyl acetate/ethylene copolymer (Vinnapas® EP 65 W, from Wacker) and 2000 g of water. The active composition was applied in the form of thin layers.

Example 3

Preparation of Catalyst C

To prepare catalyst C having an active composition content of 8% by weight and the composition of 7.5% by weight of vanadium pentoxide, 3.2% by weight of antimony trioxide, 0.2% by weight of phosphorus (calculated as phosphorus) and remainder titanium dioxide, 2200 g of steatite bodies in the form of hollow cylinders of size 8×6×5 mm were coated at a temperature of 70° C. in a fluidized bed coater with a suspension of 13.35 g of vanadium pentoxide, 5.7 g of antimony trioxide, 1.34 g of ammonium dihydrogenphosphate, 158.65 g of titanium dioxide having a BET surface area of 21 m$^2$/g, 109.4 g of binder composed of a 50% dispersion of water and vinyl acetate/ethylene copolymer (Vinnapas® EP 65 W, from Wacker) and 2000 g of water. The active composition was applied in the form of thin layers.

Example 4

Preparation of Catalyst D

To prepare catalyst D having an active composition content of 9% by weight and the composition of 7.5% by weight of vanadium pentoxide, 3.2% by weight of antimony trioxide, 0.40% by weight of caesium (calculated as caesium), 0.2% by weight of phosphorus (calculated as phosphorus) and remainder titanium dioxide, 2000 g of steatite bodies in the form of hollow cylinders of size 8×6×5 mm were coated at a temperature of 70° C. in a fluidized bed coater with a suspension of 17.0 g of vanadium pentoxide, 7.0 g of antimony trioxide, 1.1 g of caesium sulphate, 1.65 g of ammonium dihydrogenphosphate, 194.9 g of titanium dioxide having a BET surface area of 21 m$^2$/g, 102.1 g of binder composed of a 50% dispersion of water and vinyl acetate/ethylene copolymer (Vinnapas® EP 65 W, from Wacker) and 2000 g of water. The active composition was applied in the form of thin layers.

Example 5

Preparation of Catalyst E

To prepare catalyst E having an active composition content of 8% by weight and the composition of 7.5% by weight of vanadium pentoxide, 3.2% by weight of antimony trioxide, 0.20% by weight of caesium (calculated as caesium), 0.2% by weight of phosphorus (calculated as phosphorus) and remainder titanium dioxide, 2000 g of steatite bodies in the form of hollow cylinders of size 8×6×5 mm were coated at a temperature of 70° C. in a fluidized bed coater with a suspension of 15.1 g of vanadium pentoxide, 6.3 g of antimony trioxide, 0.53 g of caesium sulphate, 1.47 g of ammonium dihydrogenphosphate, 173.7 g of titanium dioxide having a BET surface area of 21 m$^2$/g, 101 g of binder composed of a 50% dispersion of water and vinyl acetate/ethylene copolymer (Vinnapas® EP 65 W, from Wacker) and 2000 g of water. The active composition was applied in the form of thin layers.

Example 6

Preparation of Catalyst F

To prepare catalyst F having an active composition content of 8% by weight and the composition of 7.5% by weight of vanadium pentoxide, 3.2% by weight of antimony trioxide, 0.2% by weight of phosphorus (calculated as phosphorus) and remainder titanium dioxide, 2000 g of steatite bodies in the form of hollow cylinders of size 8×6×5 mm were coated at a temperature of 70° C. in a fluidized bed coater with a suspension of 15.1 g of vanadium pentoxide, 6.25 g of antimony trioxide, 1.47 g of ammonium dihydrogenphosphate, 174.11 g of titanium dioxide having a BET surface area of 27 m$^2$/g, 101 g of binder composed of a 50% dispersion of water and vinyl acetate/ethylene copolymer (Vinnapas® EP 65 W, from Wacker) and 2000 g of water. The active composition was applied in the form of thin layers.

Example 7

Preparation of Catalyst G

To prepare catalyst G having an active composition content of 8% by weight and the composition of 7.5% by weight of vanadium pentoxide, 3.2% by weight of antimony trioxide, 0.2% by weight of phosphorus (calculated as phosphorus) and remainder titanium dioxide, the procedure was exactly as above in Example 6 for catalyst F, except that titanium dioxide having a BET surface area of 21 m$^2$/g was used.

Example 8

Catalytic Performance Data in the Oxidation of O-Xylene to Phthalic Anhydride

Comparative Example 1

A 450 cm-long reaction tube is charged successively with 100 cm of catalyst C, 60 cm of catalyst B and 130 cm of catalyst A. The reaction tube is disposed in a liquid salt melt which can be heated to temperatures up to 450° C. In the catalyst bed is disposed a 3 mm protective tube with an incorporated thermoelement, which can be used to indicate the catalyst temperature over the complete catalyst combination. To determine the catalytic performance data, 0 to a maximum of 70 g/m$^3$ (STP) of o-xylene (purity 99.9%) are passed at 3.6 m$^3$ (STP) of air/h over this catalyst combination in the sequence ABC, and the reaction gas, downstream of the reaction tube exit, is passed through a condenser in which all organic constituents of the reaction gas apart from the carbon monoxide and carbon dioxide are deposited. The deposited crude product is melted off by means of superheated steam, collected and subsequently weighed.

The crude yield is determined as follows.

Max. crude PA yield[by weight]=Weighed amount of crude PA[g]×100/feed of o-xylene[g]×purity of o-xylene[%/100]

In a further test (Example 8a) the lengths of the zones were varied as follows: 90 cm catalyst C, 60 cm catalyst B, 140 cm catalyst A. Otherwise, the procedure is as described under Example 8.

The results of the test run are listed in Table 1.

Example 9

Catalytic Performance Data in the Oxidation of O-Xylene to Phthalic Anhydride

Inventive Example 1

A 450 cm-long reaction tube is charged successively with 90 cm of catalyst F, 60 cm of catalyst E and 140 cm of catalyst D. Otherwise, the procedure is as described under Example 8. The results of the test run are listed in Table 1.

Example 10

Catalytic Performance Data in the Oxidation of O-Xylene to Phthalic Anhydride

Comparative Example 2

A 450 cm-long reaction tube is charged successively with 130 cm of catalyst C, 60 cm of catalyst B and 100 cm of catalyst A. Otherwise, the procedure is as described under Example 8. The results of the test run are listed in Table 1.

Example 11

Catalytic Performance Data in the Oxidation of O-Xylene to Phthalic Anhydride

Inventive Example 2

A 450 cm-long reaction tube is charged successively with 90 cm of catalyst G, 60 cm of catalyst E and 140 cm of catalyst D. Otherwise, the procedure is as described under Example 8. The results of the test run are listed in Table 1.

highest PA quality. The hotspot is advantageously positioned in the first catalyst zone. Inventive Example 9, in which the BET surface area increases from the first to the third catalyst zone (here: is higher in the third catalyst zone than in the first and second catalyst zone), is even better with regard to the PA quality than Inventive Example 11, in which the BET surface area does not rise from the first toward the third catalyst zone.

In the following Examples, the only feature that was changed was the active composition content in the specific zones.

Example 12

Comparative Example

Catalysts Used:
Zone 1: Catalyst H, 9% by weight active composition content
Zone 2: Catalyst I, 10% by weight active composition content
Zone 3: Catalyst J, 11% by weight active composition content To prepare catalyst H having an active composition content of 9% by weight and the composition of 7.5% by weight of vanadium pentoxide, 3.2% by weight of antimony trioxide, 0.40% by weight caesium (calculated as caesium), 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 20.3 g of vanadium pentoxide, 8.7 g of antimony trioxide, 1.5 g of caesium sulfate, 2.0 g of ammonium dihydrogenphosphate, 240.1 g of titanium dioxide having a BET surface area of 21 m$^2$/g, 132.1 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst I having an active composition content of 10% by weight and the composition of 7.5% by weight of vanadium pentoxide, 3.2% by weight of antimony trioxide, 0.20% by weight caesium (calculated as caesium), 0.2% by weight of phosphorus (calculated as phosphorus) and remainder titanium dioxide, 2600 g of steatite bodies in the form of

TABLE 1

| Example | Maximum loading | Crude PA yield | PA quality (phthalide value in the reaction gas) | Hotspot temperature and location |
| --- | --- | --- | --- | --- |
| Example 8: Catalyst combination A (130 cm) B (60 cm) C (100 cm) | 50 g/Nm$^3$ | 112.4% by wt. | >2000 ppm | 450° C. 150 cm (2nd zone) |
| Example 8a: Catalyst combination A (140 cm) B (60 cm) C (90 cm) | 54 g/Nm$^3$ | 112.6% by wt. | >2200 ppm | 447° C. 150 cm (2$^{nd}$ zone) |
| Example 9: Catalyst combination D (140 cm) E (60 cm) F (90 cm) | 57 g/Nm$^3$ | 113.8% by wt. | <500 ppm | 440° C. 50 cm (1st zone) |
| Example 10: Catalyst combination A (100 cm) B (60 cm) C (130 cm) | 45 g/Nm$^3$ | 106.7% by wt. | >10000 ppm | 450° C. 150 cm (2nd zone) |
| Example 11: Catalyst combination D (140 cm) E (60 cm) G (90 cm) | 58 g/Nm$^3$ | 113.6% by wt. | <800 ppm | 440° C. 50 cm (1st zone) |

As can be seen from Table 1, the inventive catalysts according to Examples 9 and 11 show the highest PA yield and hollow cylinders of size 8×6×5 mm were coated at a temperature of 70° C. in a fluidized bed coater with a suspension of 22.8 g of vanadium pentoxide, 9.7 g of antimony trioxide, 0.8 g of caesium sulfate, 2.3 g of ammonium dihydrogenphosphate, 270.3 g of titanium dioxide having a BET surface area of 21 m$^2$/g, 133.6 g of binder composed of a 50% dispersion of water and vinyl acetate/ethylene copolymer (Vinnapas® EP 65 W, from Wacker) and 2300 g of water. The active composition was applied in the form of thin layers.

To prepare catalyst J having an active composition content of 11% by weight and the composition of 7.5% by weight of vanadium pentoxide, 3.2% by weight of antimony trioxide, 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 25.4 g of vanadium pentoxide, 10.8 g of antimony trioxide, 2.5 g of ammonium dihydrogenphosphate, 301.4 g of titanium dioxide having a BET surface area of 27 m$^2$/g, 135.2 g of binder composed of a 50% dispersion of water and vinyl acetate/ethylene copolymer (Vinnapas® EP 65 W, from Wacker) and 2500 g of water. The active composition was applied in the form of thin layers.

Example 13

Inventive Example

Catalysts Used:
Zone 1: Catalyst K, 9% by weight active composition content
Zone 2: Catalyst L, 8% by weight active composition content
Zone 3: Catalyst M, 7% by weight active composition content To prepare catalyst K having an active composition content of 9% by weight and the composition of 7.5% by weight of vanadium pentoxide, 3.2% by weight of antimony trioxide, 0.40% by weight caesium (calculated as caesium), 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 20.3 g of vanadium pentoxide, 8.7 g of antimony trioxide, 1.5 g of caesium sulfate, 2.0 g of ammonium dihydrogenphosphate, 240.1 g of titanium dioxide having a BET surface area of 21 m$^2$/g, 132.1 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst L having an active composition content of 8% by weight and the composition of 7.5% by weight of vanadium pentoxide, 3.2% by weight of antimony trioxide, 0.20% by weight caesium (calculated as caesium), 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 17.9 g of vanadium pentoxide, 7.6 g of antimony trioxide, 0.6 g of caesium sulfate, 1.8 g of ammonium dihydrogenphosphate, 211.6 g of titanium dioxide having a BET surface area of 21 m$^2$/g, 132.1 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst M having an active composition content of 7% by weight and the composition of 7.5% by weight of vanadium pentoxide, 3.2% by weight of antimony trioxide, 0.2% by weight of phosphorus (calculated as phosphorus) and remainder titanium dioxide, 2600 g of steatite bodies in the form of hollow cylinders of size 8×6×5 mm were coated at a temperature of 70° C. in a fluidized bed coater with a suspension of 15.5 g of vanadium pentoxide, 6.6 g of antimony trioxide, 1.6 g of ammonium dihydrogenphosphate, 183.5 g of titanium dioxide having a BET surface area of 27 m$^2$/g, 129.1 g of binder composed of a 50% dispersion of water and vinyl acetate/ethylene copolymer (Vinnapas® EP 65 W, from Wacker) and 1800 g of water. The active composition was applied in the form of thin layers.

The 3-zone-catalysts of Examples 12 and 13 were used as follows:

A 450 cm-long reaction tube is charged with 150 cm of catalyst H (Example 12) and K (Example 13), respectively, 60 cm of catalyst I (Example 12) and L (Example 13), respectively, and 80 cm of catalyst J (Example 12) and M (Example 13), respectively. Otherwise, the procedure is as described under Example 8. The results of the test run are listed in Table 2.

TABLE 2

| Example | Maximum loading | Crude PA yield | Hotspot temperature and location |
|---|---|---|---|
| 12 (Comparative Example): Catalyst combination H (150 cm) I (60 cm) J (80 cm) | 60 g/Nm$^3$ | 109.4% by wt. | 448° C. 55 cm (1st zone) |
| 13 (Inventive Example): Catalyst combination K (150 cm), L (60 cm) M (80 cm) | 60 g/Nm$^3$ | 114.1% by wt. | 450° C. 55 cm (1st zone) |

As can be seen from Table 21 the inventive 3-zone-catalyst according to Example 13 shows a much higher PA yield.

Example 14

Comparative Example

Catalysts Used:
Zone 1: Catalyst N, 8% by weight active composition content
Zone 2: Catalyst O, 9% by weight active composition content
Zone 3: Catalyst P, 10% by weight active composition content To prepare catalyst N having an active composition content of 8% by weight and the composition of 7.5% by weight of vanadium pentoxide, 3.2% by weight of antimony trioxide, 0.40% by weight caesium (calculated as caesium) and remainder titanium dioxide, 2600 g of steatite bodies in the form of hollow cylinders of size 8×6×5 mm were coated at a temperature of 70° C. in a fluidized bed coater with a suspension of 17.9 g of vanadium pentoxide, 7.6 g of antimony trioxide, 1.3 g of caesium sulfate, 211.6 g of titanium dioxide having a BET surface area of 21 m$^2$/g, 130.5 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst O having an active composition content of 9% by weight and the composition of 7.5% by weight of vanadium pentoxide, 3.2% by weight of antimony trioxide, 0.20% by weight caesium (calculated as caesium) and remainder titanium dioxide, 2600 g of steatite bodies in the form of hollow cylinders of size 8×6×5 mm were coated at a temperature of 70° C. in a fluidized bed coater with a suspension of 20.3 g of vanadium pentoxide, 8.7 g of antimony trioxide, 0.7 g of caesium sulfate, 241.2 g of titanium dioxide having a BET surface area of 21 m$^2$/g, 132.1 g of binder composed of a 50% dispersion of water and vinyl acetate/ ethylene copolymer (Vinnapas® EP 65 W, from Wacker) and 2300 g of water. The active composition was applied in the form of thin layers.

To prepare catalyst P having an active composition content of 10% by weight and the composition of 7.5% by weight of vanadium pentoxide, 0.2% by weight phosphorous (calculated as phosphorous) and remainder titanium dioxide, 2600 g of steatite bodies in the form of hollow cylinders of size 8×6×5 mm were coated at a temperature of 70° C. in a fluidized bed coater with a suspension of 22.8 g of vanadium pentoxide, 2.3 g of ammonium dihydrogenphosphate, 280.7 g of titanium dioxide having a BET surface area of 27 m²/g, 133.6 g of binder composed of a 50% dispersion of water and vinyl acetate/ethylene copolymer (Vinnapas® EP 65 W, from Wacker) and 2500 g of water. The active composition was applied in the form of thin layers.

Example 15

Inventive Example

Catalysts Used:
Zone 1: Catalyst Q, 8% by weight active composition content
Zone 2: Catalyst R, 8% by weight active composition content
Zone 3: Catalyst S, 7% by weight active composition content To prepare catalyst Q having an active composition content of 8% by weight and the composition of 7.5% by weight of vanadium pentoxide, 3.2% by weight of antimony trioxide, 0.40% by weight caesium (calculated as caesium) and remainder titanium dioxide, 2600 g of steatite bodies in the form of hollow cylinders of size 8×6×5 mm were coated at a temperature of 70° C. in a fluidized bed coater with a suspension of 17.9 g of vanadium pentoxide, 7.6 g of antimony trioxide, 1.3 g of caesium sulfate, 211.6 g of titanium dioxide having a BET surface area of 21 m²/g, 130.5 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst R having an active composition content of 8% by weight and the composition of 7.5% by weight of vanadium pentoxide, 3.2% by weight of antimony trioxide, 0.20% by weight caesium (calculated as caesium) and remainder titanium dioxide, 2600 g of steatite bodies in the form of hollow cylinders of size 8×6×5 mm were coated at a temperature of 70° C. in a fluidized bed coater with a suspension of 17.9 g of vanadium pentoxide, 7.6 g of antimony trioxide, 0.6 g of caesium sulfate, 212.1 g of titanium dioxide having a BET surface area of 21 m²/g, 130.5 g of binder composed of a 50% dispersion of water and vinyl acetate/ethylene copolymer (Vinnapas® EP 65 W, from Wacker) and 2000 g of water. The active composition was applied in the form of thin layers.

To prepare catalyst S having an active composition content of 7% by weight and the composition of 7.5% by weight of vanadium pentoxide, 0.2% by weight phosphorous (calculated as phosphorous) and remainder titanium dioxide, 2600 g of steatite bodies in the form of hollow cylinders of size 8×6×5 mm were coated at a temperature of 70° C. in a fluidized bed coater with a suspension of 15.5 g of vanadium pentoxide, 1.6 g of ammonium dihydrogenphosphate, 190.1 g of titanium dioxide having a BET surface area of 27 m²/g, 129.1 g of binder composed of a 50% dispersion of water and vinyl acetate/ethylene copolymer (Vinnapas® EP 65 W, from Wacker) and 1800 g of water. The active composition was applied in the form of thin layers.

The 3-zone-catalysts of Examples 14 and 15 were used as follows:

A 450 cm-long reaction tube is charged with 160 cm of catalyst N (Example 14) and Q (Example 15), respectively, 60 cm of catalyst O (Example 14) and R (Example 15), respectively, and 70 cm of catalyst P (Example 14) and S (Example 15), respectively. Otherwise, the procedure is as described under Example 8. The results of the test run are listed in Table 3.

The invention claimed is:

1. Catalysts for preparing phthalic anhydride by gas phase oxidation of o-xylene and/or naphthalene, comprising a first catalyst zone disposed toward a gas inlet side, a second catalyst zone disposed closer to a gas outlet side and a third catalyst zone disposed even closer to or at the gas outlet side, the catalyst zones having different compositions, wherein the composition of each catalyst zone comprises an active composition comprising $TiO_2$ with a content of Na of less than 0.3% by weight, wherein the active composition content decreasing from the first catalyst zone to the third catalyst zone, and wherein
    a) the first catalyst zone has an active composition content between about 7 and 12% by weight,
    b) the second catalyst zone has an active composition content between 6 and 11% by weight, wherein the active composition content of the second catalyst zone is less than or equal to the active composition content of the first catalyst zone, and
    c) the third catalyst zone has an active composition content in the range between 5 and 10% by weight, wherein the active composition content of the third catalyst zone is less than or equal to the active composition content of the second catalyst zone.

2. The catalysts according to claim 1, characterized in that the first catalyst zone has an active composition content between about 8 and 11% by weight.

3. The catalysts according to claim 1, characterized in that the second catalyst zone has an active composition content between about 7 and 10% by weight.

4. The catalysts according to claim 1, characterized in that the third catalyst zone has an active composition content between about 6 and 9% by weight.

5. The catalysts according to claim 1, characterized in that the active composition content decreases from catalyst zone to catalyst zone in the direction of the gas flow.

6. The catalysts according to claim 1, wherein the catalysts further comprise a Cs-content, characterized in that the Cs-content (calculated as Cs) decreases from catalyst zone to catalyst zone in the direction of the gas flow.

7. The catalysts according to claim 1, characterized in that only the catalyst zone closest to the outlet side contains phosphorous in an amount between 0.01 and 0.5% by weight, (calculated as phosphorous).

8. The catalysts according to claim 1, characterized in that the catalyst activity of the catalyst zone toward the gas inlet side is lower than the catalyst activity of the catalyst zone toward the gas outlet side.

9. The catalysts according to claim 1, characterized in that the BET surface area of the first catalyst zone is lower than the BET surface area of the third catalyst zone.

10. The catalysts according to claim 1, characterized in that the BET surface area of the first and of the second catalyst zone is the same, while the BET surface area of the third catalyst zone is greater in comparison.

11. The catalysts according to claim 1, characterized in that the BET surface area of the first and second catalyst zone is in each case between about 15 and 25 m²/g, and the BET surface area of the third catalyst zone is between about 25 and 45 m²/g.

12. The catalysts according to claim 1, characterized in that the first catalyst zone disposed toward the gas inlet side has a length fraction, based on the total length of the catalyst bed, of at least 40%.

13. The catalysts according to claim 1, characterized in that the proportion of the first catalyst zone in the total length of the catalyst bed is between 40 and 70%.

14. The catalysts according to claim 1, characterized in that the proportion of the second catalyst zone in the total length of the catalyst bed is between about 10 and 40%.

15. The catalysts according to claim 1, characterized in that the ratio of the length of the third catalyst zone to the length of the second catalyst zone is between about 1 and 2.

16. The catalysts according to claim 1, characterized in that at least about 40%, of the total pore volume of the $TiO_2$ used is formed by pores having a radius between 60 and 400 nm.

17. The catalysts according to claim 1, characterized in that up to 75%, of the total pore volume of the $TiO_2$ used is formed by pores having a radius between 60 and 400 nm.

18. The catalysts according to claim 1, characterized in that the catalytically active composition is applied in a moving bed or fluidized bed.

19. The catalysts according to claim 1, characterized in that less than about 30%, of the total pore volume of the $TiO_2$ is formed by pores having a radius of more than 400 nm.

20. The catalysts according to claim 1, characterized in that about 17 to 27% of the total pore volume of the $TiO_2$ is formed by pores having a radius of more than 400 nm.

21. The catalysts according to claim 1, characterized in that about 50 to 75%, of the total pore volume of the $TiO_2$ is formed by pores having a radius of 60 to 400 nm.

22. The catalysts according to claim 1, characterized in that less than 30%, of the total pore volume of the $TiO_2$ is formed by pores having a radius of 3.7 to 60 nm.

23. The catalysts according to claim 1, characterized in that about 10 to 30% of the total pore volume of the $TiO_2$ is formed by pores having a radius of 3.7 to 60 nm.

24. The catalysts according to claim 1, characterized in that the $D_{90}$ value of the $TiO_2$ is between about 0.5 and 20 µm.

25. The catalysts according to claim 1, characterized in that less than 10%, of the total pore volume of the $TiO_2$ is present by virtue of micropores having a pore radius of less than 3.7 nm.

26. The catalysts according to claim 1, characterized in that 8% by weight or more of the catalytically active composition comprises vanadium, calculated as vanadium pentoxide.

27. The catalysts according to claim 1, characterized in that at least 0.05% by weight of the catalytically active composition is formed from at least one alkali metal, calculated as alkali metal(s).

28. The catalysts according to claim 1, characterized in that an adhesive used with the catalytically active composition comprises an organic polymer or copolymer.

29. The catalysts according to claim 1, calcined or conditioned in an $O_2$-containing gas, at >390° C. for at least 24 hours.

30. The catalysts according to claim 1, wherein the active composition further comprising niobium in an amount of 0.1 to 2% by weight.

31. The catalysts according to claim 1, characterized in that only one $TiO_2$ source is used.

32. The catalysts according to claim 1, characterized in that no phosphorus is present in the active composition.

* * * * *